United States Patent
Cai et al.

(10) Patent No.: US 9,709,730 B2
(45) Date of Patent: Jul. 18, 2017

(54) HOLLOW-CORE PHOTONIC CRYSTAL FIBER GAS CELL AND METHOD FOR PREPARING THE SAME

(71) Applicant: Shanghai Institute of Optics And Fine Mechanics, Chinese Academy of Sciences, Shanghai (CN)

(72) Inventors: Haiwen Cai, Shanghai (CN); Zeheng Chen, Shanghai (CN); Fei Yang, Shanghai (CN); Jianxin Geng, Shanghai (CN); Dijun Chen, Shanghai (CN); Weibiao Chen, Shanghai (CN)

(73) Assignee: Shanghai Institute of Optics And Fine Mechanics, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/393,163

(22) Filed: Dec. 28, 2016

(65) Prior Publication Data

US 2017/0108641 A1    Apr. 20, 2017

Related U.S. Application Data

(63) Continuation-in-part of application No. PCT/CN2014/083684, filed on Aug. 5, 2014.

(30) Foreign Application Priority Data

Jul. 7, 2014   (CN) .......................... 2014 1 0321070

(51) Int. Cl.
*G02B 6/44* (2006.01)
*G02B 6/02* (2006.01)
(Continued)

(52) U.S. Cl.
CPC ......... *G02B 6/02323* (2013.01); *G01N 21/03* (2013.01); *G02B 6/255* (2013.01); *G01N 2201/0846* (2013.01)

(58) Field of Classification Search
CPC ... G02B 6/4484; G02B 6/4488; G02B 6/4463
See application file for complete search history.

(56) References Cited

U.S. PATENT DOCUMENTS

| | | | |
|---|---|---|---|
| 6,249,343 B1 | 6/2001 | Wang et al. | |
| 9,372,299 B1 * | 6/2016 | Yi | .......................... H01J 65/042 |
| 2008/0037939 A1 * | 2/2008 | Xiao | .................. G02B 6/02376 |
| | | | 385/96 |

FOREIGN PATENT DOCUMENTS

| | | |
|---|---|---|
| CN | 1648637 A | 8/2005 |
| CN | 1900696 A | 1/2007 |
| (Continued) | | |

OTHER PUBLICATIONS

Benabid, F., et al., "Compact, stable and efficient all-fibre gas cells using hollow-core photonic crystal fibres," Nature, 2005,434 (7032): 488-491 (2005).

(Continued)

*Primary Examiner* — Sung Pak
*Assistant Examiner* — Hoang Tran
(74) *Attorney, Agent, or Firm* — Mei & Mark LLP; Manni Li

(57) ABSTRACT

A hollow-core photonic crystal fiber gas cell and method for preparing the same. The hollow-core photonic crystal fiber gas cell comprises a single-mode fiber, a fiber splicing protection sleeve, a hollow-core photonic crystal fiber, and a photoelectric detector. One end of the single-mode fiber is fusion spliced with one end of the hollow-core photonic crystal fiber to form a fusion splice and seal one end of the hollow-core photonic crystal fiber gas cell. The fiber splicing protection sleeve covers and protects the fusion splice. The other end of the hollow-core photonic crystal fiber is processed into an output end by fusion sealing, and the surface (Continued)

of the output end faces, but is not parallel to, a detection surface of the photoelectric detector.

2 Claims, 4 Drawing Sheets

(51) Int. Cl.
*G01N 21/03* (2006.01)
*G02B 6/255* (2006.01)

(56) References Cited

FOREIGN PATENT DOCUMENTS

| CN | 101419161 A | 4/2009 |
|---|---|---|
| CN | 102866468 A | 1/2013 |

OTHER PUBLICATIONS

Couny, F., et al., "Reduction of Fresnel Back-Reflection at Splice Interface Between Hollow Core PCF and Single-Mode Fiber," IEEE Photonics Technology Letters, 2007, 19(13): 1020-1022.
Marty, P.T., et al., "All-Fiber Multi-Purpose Gas Cells and Their Applications in Spectroscopy," Journal of Lightwave Technology, 2010, 28(8): 1236-1240.

\* cited by examiner

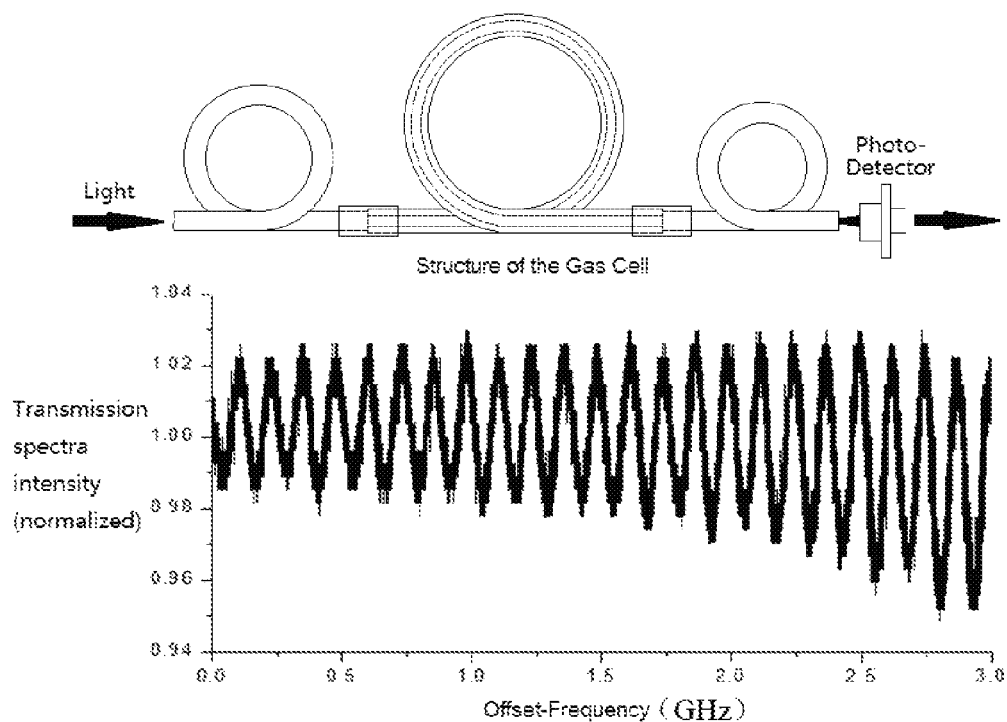
Figure 6(a)
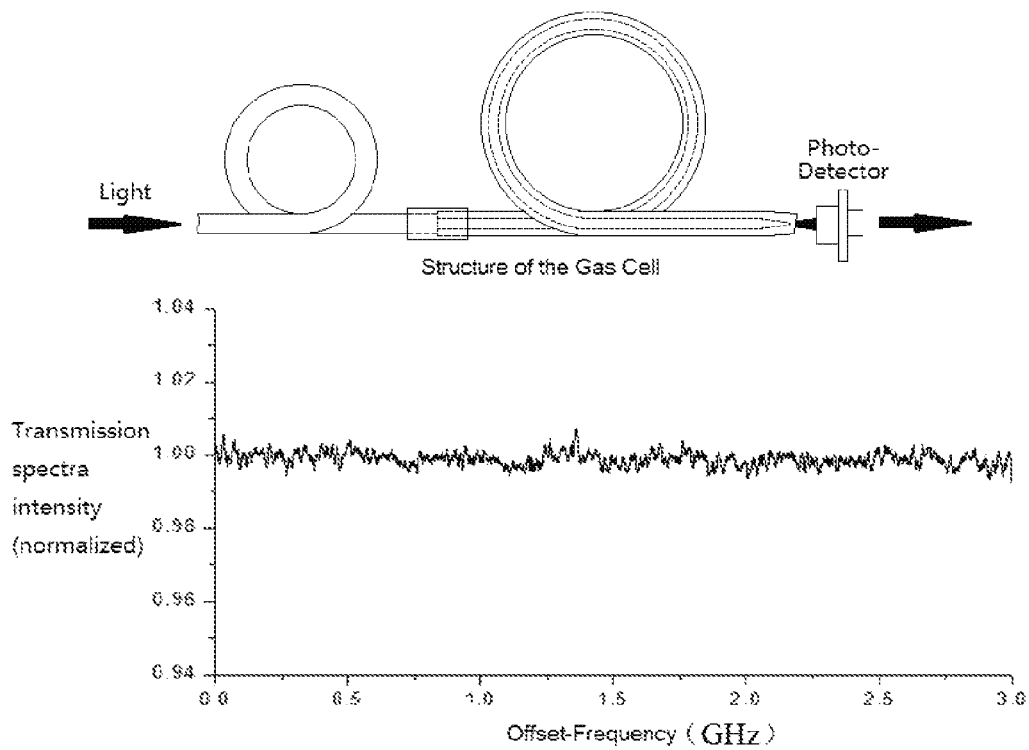
Figure 6(b)
Figure 6

HOLLOW-CORE PHOTONIC CRYSTAL FIBER GAS CELL AND METHOD FOR PREPARING THE SAME

CROSS-REFERENCE TO RELATED APPLICATIONS

The subject application is a continuation-in-part of PCT/CN2014/083684 filed on August 5, 2014, which claims priority on Chinese patent application 201410321070.7 filed on Jul. 7, 2014 in China. The contents and subject matter of the PCT international application and Chinese priority application are incorporated herein by reference.

FIELD OF THE INVENTION

The present invention relates to the gas cell, particularly, a hollow-core photonic crystal fiber gas cell and method for preparing the same.

DESCRIPTION OF THE RELATED ART

A laser with certain frequency and high stability is required in the fields of gas absorption spectrum analysis, laser frequency stabilization, cold atomic clocks, et al. A tunable diode laser with frequency stabilization using the gas absorption line as the frequency reference is used for the purpose.

The gas cell is an essential component in the laser for gas absorption line based frequency stabilization. The length of the reference cell is required to be extensive in order to get enough absorption when the absorption of some gas line is very weak. Moreover, the gas cell is required to have small volume, light weight, and high stability in order to meet the weight and vibration resistance requirements for the frequency stabilization laser applied in the space-borne, airborne, and on-vehicle fields.

It is known that the use of hollow-core photonic crystal fiber may help achieve a small size, light weight, and highly robustness gas absorption cell. In the gas cells, the hollow-core photonic crystal fiber is filled with a designated gas. Then, the gas cell is completed by connecting two ends of the hollow-core photonic crystal fiber with the single-mode optical fiber via fusion splicing. See [I] Benabid, F., et al. "Compact, stable and efficient all-fibre gas cells using hollow-core photonic crystal fibres," Nature, 2005, 434 (7032): 488-491 (2005). However, significant Fresnel reflection occurs on the interface between the hollow-core photonic crystal fiber and the single mode optic fiber, because the surface of the splicing interface is vertically paralleled. According to the theory of the Fabry-Pérot interferometer, as the two end surfaces of the hollow-core photonic crystal fiber gas cell are splicing surfaces in parallel vertically, the gas cell easily forms a Fabry-Pérot resonant cavity. Thus, the transmission spectrum of the hollow-core photonic crystal fiber gas cell contains the Fabry-Pérot interference fringe. Solution to the problem in the prior art includes using angle cleaved fibers, spliced together using a filament fusion splicer. See [II] Couny, F., et al., "Reduction of Fresnel Back-Reflection at Splice Interface Between Hollow Core PCF and Single-Mode Fiber," IEEE Photonics Technology Letters, 2007, 19(13): 1020-1022. However, it is very difficult to cleave the hollow-core photonic crystal fiber with slant angles, thus, the method is difficult to implement.

Another known hollow-core photonic crystal fiber gas absorption cell aligns the hollow-core photonic crystal fiber with the silicon-based V-groove of a multi-purpose photonic fiber to achieve optical coupling. See [III] Marty, P. T., et al., "All-Fiber Multi-Purpose Gas Cells and Their Applications in Spectroscopy," Journal of Lightwave Technology, 2010, 28(8): 1236-1240. However, a multi-mode light field exists in the hollow-core photonic crystal fiber due to the specific structure of the hollow-core photonic crystal fiber and limitation on the manufacture method, which further causes the change in distribution of the far-field light spots by the multi-mode interference. When in use, the centroid of far-field light spots consecutively change as caused by the mode interference.

In these prior arts ([I], [II], and [III]) which use fusion splicing or adapting the output end of the hollow-core photonic crystal fiber with the single mode optic fiber have one common problem: the finite fiber core diameter between the single mode optic fiber and the hollow-core photonic crystal fiber equals to adding a space filter into the gas cells, which will cause additional background oscillations that make the frequency stability deteriorated.

Therefore, the existing technology needs to be improved and new technology developed.

SUMMARY OF THE INVENTION

The present invention overcomes the disadvantages of the prior art and provides a hollow-core photonic crystal fiber gas cell and method for preparing the same. The hollow-core photonic crystal fiber gas cell eliminates the Fabry-Pérot interference fringes in the background noise of the transmission spectrum and reduces the corresponding background noise oscillations in the transmission spectrum.

The present invention achieves the goal through the following:

The hollow-core photonic crystal fiber gas cell comprises a single-mode fiber, a fiber splicing protection sleeve, a hollow-core photonic crystal fiber, and a photoelectric detector; one end of the single-mode optic fiber is coupled to one end of the hollow-core photonic crystal fiber via fusion splicing to form a fusion splice and a sealed end of the hollow-core photonic crystal fiber gas cell; the fusion splice is covered and protected by the fiber splicing protection sleeve. The hollow-core photonic crystal fiber gas cell is characterized in that the other end of the hollow-core photonic crystal fiber is processed into an output end in a fusion sealing manner, and the output end surface faces, but is not parallel to, the detection surface of the photoelectric detector.

The present invention further provides a method for preparing the gas cell as follows:

(1) connecting the input end of the hollow-core photonic crystal fiber with the output end of the single mode optic fiber via fusion splicing to form a fusion splice and sealing one end of the hollow-core photonic crystal fiber and covering the fusion splice with an optic fiber splicing protection sleeve for protection.

(2) placing the hollow-core photonic crystal fiber spliced to the single mode optic fiber in a vacuum chamber, and filling the hollow-core of the hollow-core photonic crystal fiber in the vacuum chamber with gas.

(3) causing the free end of the hollow-core photonic crystal fiber to collapse by fusing in the gas chamber and sealing the gas in the hollow-core of the hollow-core photonic crystal fiber and forming a collapsed end of the hollow-core photonic crystal fiber.

(4) treating the collapsed end of the hollow-core photonic crystal fiber as follows:

First, a signal light enters through the free end of the single mode optic fiber, then the transmitted light comes out from the collapsed end; the transmitted light is detected by the photodetector and the detected signal is recorded by an instrument.

Second, the collapsed end of the hollow-core photonic crystal fiber is polished, cut, or coated with a membrane, so that the detected signal matches the requirements of the system. The after-machining collapsed end becomes the output end of the hollow-core photonic crystal fiber.

(5) fixing the device comprising the output end of the hollow-core photonic crystal fiber and the photodetector.

The gas cell of the present invention has the following advantages over the existing technology:

(1) Compared with reference [I], the collapsed end of the hollow-core photonic crystal fiber is polished, cut, or coated with a membrane, after forming the collapsed end, which reduces the Fabry-Pérot fringes in the background oscillations in the transmission spectrum.

(2) Compared with reference [II], the treatment of the collapsed end of the hollow-core photonic crystal fiber being polished, cut, or coated with a membrane, after forming the collapsed end, is simple, convenient, easy to realize and repeated.

(3) Compared with references [I], [II], and [III], one end of the hollow-core photonic crystal fiber gas cell have been well fixed with the photonic detector after the collapse treatment, which prevents the space filter effect caused by the coupling of the optic fiber with the finite fiber core diameter and decreases the background oscillations in the transmission spectrum.

BRIEF DESCRIPTION OF THE DRAWINGS

FIG. 6 shows comparison of the transmission spectrum of the present invention and that of a common hollow-core photonic crystal fiber gas cell in the prior art: FIG. 6(a) shows the structure of the gas cell of the prior art and corresponding transmission spectrum; FIG. 6(b) shows the structure of the gas cell of the present invention and corresponding transmission spectrum.

These drawings are for illustration only and are not drawn in proportion. Accordingly, same components are marked with same reference numbers.

DETAILED DESCRIPTION OF THE INVENTION AND EMBODIMENTS

The present invention is further described in details, but the description does not serve to limit the scope of the invention.

Figure 1:
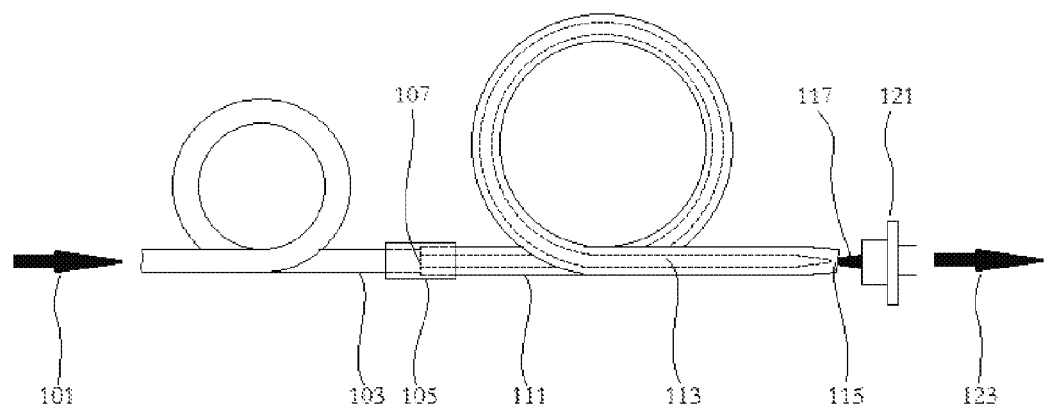
FIG. 1 shows the structure of the hollow-core photonic crystal fiber gas cell of the present invention.

As shown in FIG. 1, the hollow-core photonic crystal fiber gas cell of the present invention comprises a single-mode fiber 103, a optic fiber splicing protection sleeve 105, a hollow-core photonic crystal fiber 111, and a photoelectric detector 121. One end of the single-mode fiber 103 is fused with one end of the hollow-core photonic crystal fiber 111 so that a fusion splice 107 is formed and one end of a sealed hollow-core photonic crystal fiber gas cell is formed. The fiber splicing protection sleeve 105 protects the fusion splice 107 in a covering manner. The hollow-core photonic crystal fiber gas cell is characterized in that the other end of the hollow-core photonic crystal fiber 111 is processed into an output end 115 in a fusion sealing manner. An output end surface faces, but is not parallel to, a detection surface of the photoelectric detector 121.

The method for making the hollow-core photonic crystal fiber gas cell is characterized in the following steps:

1) One end of the single-mode fiber 103 is fusion spliced with one end of the hollow-core photonic crystal fiber 111 so that a fusion splice 107 is formed and the end of the hollow-core photonic crystal fiber gas cell is sealed air-tight. The fiber splicing protection sleeve 105 protects the fusion splice 107 in a covering manner.

2) The hollow-core photonic crystal fiber 111 and the single-mode fiber 103 that it has been spliced to are placed in the vacuum chamber, where the hollow-core 113 of the hollow-core photonic crystal fiber is filled with gas.

3) After being filled with gas, the free end of the hollow-core photonic crystal fiber 111 is collapsed by fusing in the gas chamber so that the gas is sealed in the hollow-core 113.

4) The collapsed end of the hollow-core photonic crystal fiber 111 is processed by following steps:

(i) The signal light 101 comes into the free end of the single-mode fiber 103, then the transmitted light 117 comes out of the collapsed end of the hollow-core photonic crystal fiber 111 and is detected by the photodetector 121; and the detecting signal 123 from the photodetector 121 is recorded by instrument.

(ii) The collapsed end of the hollow-core photonic crystal fiber 111 is polished, cut, coated with membrane, in order to make the detecting signal 123 to meet the requirements of the system. The after machining collapsed end is the output end 115 of the hollow-core photonic crystal fiber 111.

5) The device comprises the output end 115 of the hollow-core photonic crystal fiber 111 and the photodetector 121 are fixed on a base plate.

Figure 2:
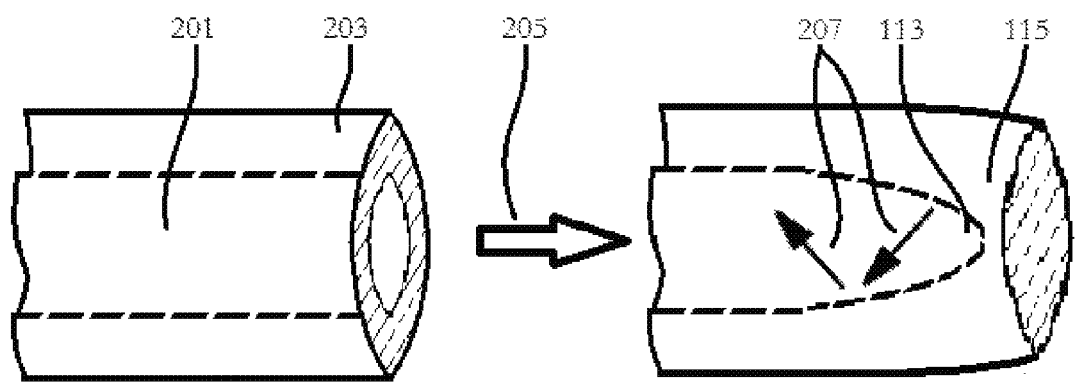
FIG. 2 shows the processing of the collapsed end of the hollow-core photonic crystal fiber in the present invention.

FIG. 2 shows the treatment effects of the output end of the hollow-core photonic crystal fiber. The left side of the Figure shows untreated hollow-core photonic crystal fiber having an open core 201. The right side of the Figure shows the hollow-core photonic crystal fiber after heat treatment process 205 on the output end 203. It shows that the output end 115 of the hollow-core photonic crystal fiber has been sealed with optic fiber layer coverage and collapsed to seal, and the hollow-core 113 of the hollow-core photonic crystal fiber forms a seal cavity, while the output end 115 forms a complete surface which may be further processed.

The heat treatment process 205 as shown in FIG. 2 uses a $CO_2$ laser or fusion splicer to heat. The end of hollow-core photonic crystal fiber is collapsed to form a non-planarity inside surface which prevents the Fabry-Pérot fringes that may be caused by the reflection and scattered light 207, and the transmission spectrum noise is decreased as well.

Figure 3:
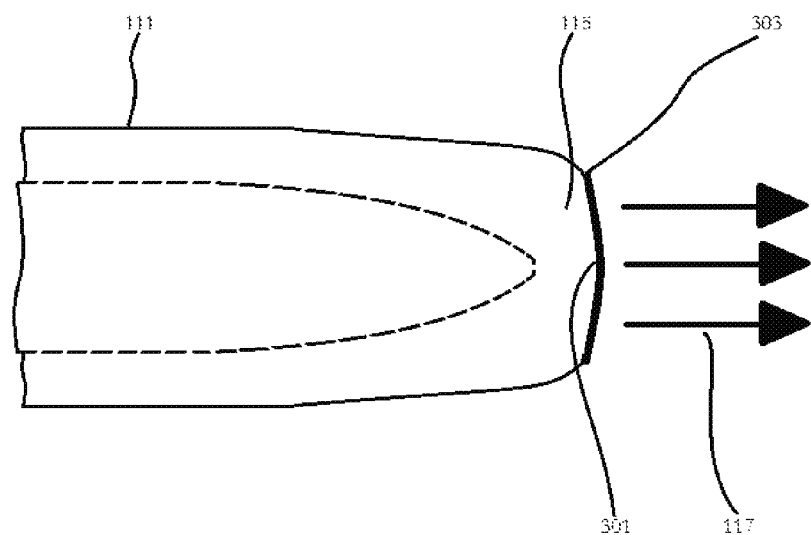
FIG. 3 shows the output end of the hollow-core photonic crystal fiber in the first embodiment of the present invention.

FIG. 3 shows a first embodiment of the hollow-core photonic crystal fiber gas cell of the present invention. The figure partially shows the output end 115 of the hollow-core photonic crystal fiber 111. In the embodiment, the output end 115 has been polished to form a surface 301 with a particular shape that may focus the transmission light 117 to be parallel. The surface 301 has also treated with an anti-reflective 303 coating.

Figure 4:
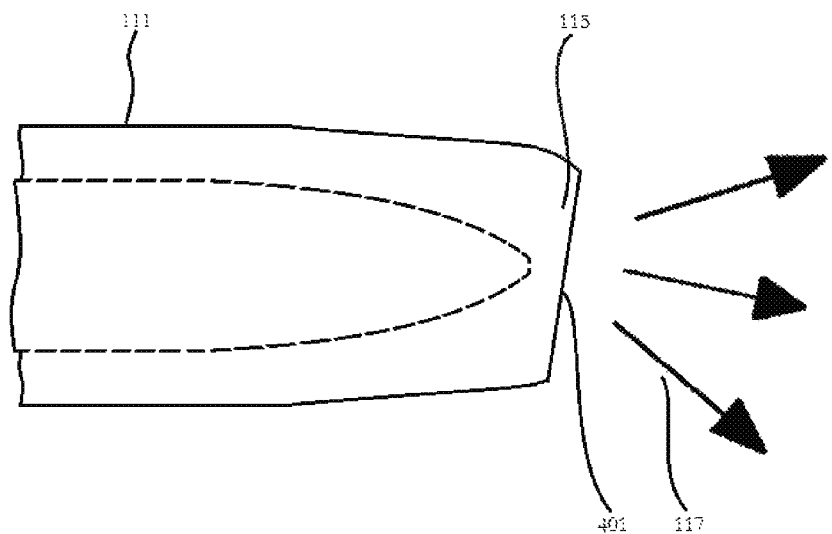
FIG. 4 shows the output end of the hollow-core photonic crystal fiber in the second embodiment of the present invention.

FIG. 4 shows a second embodiment of the hollow-core photonic crystal fiber gas cell of the present invention. The figure illustrates the output end 115 of the hollow-core photonic crystal fiber 111. In the embodiment, the output end 115 has been cut in a slant angle to form a tilted surface 401, which reduces reflection light from the surface of output end 115, and further reduces background oscillations caused by the Fabry-Pérot fringes in the transmission spectrum.

Figure 5:
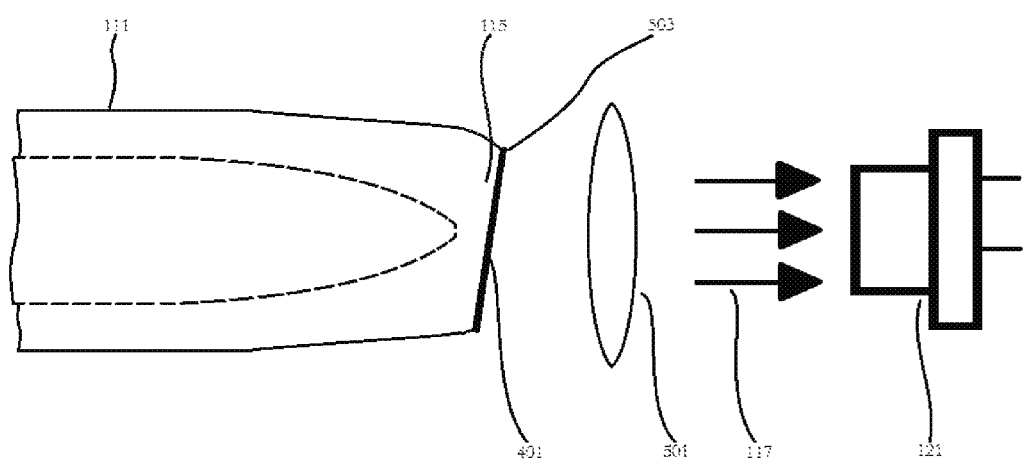
FIG. 5 shows the output end of the hollow-core photonic crystal fiber in the third embodiment of the present invention.

FIG. 5 shows a third embodiment of the hollow-core photonic crystal fiber gas cell of the present invention. The Figure partially shows the output end 115 of the hollow-core photonic crystal fiber 111 and a focusing lens 501. In the embodiment, the output end 115 has been cut at an angle on the surface to form a tilted surface 401 and then the tilted surface 401 is coated with an anti-reflective coating 503. The focusing lens 501 is fixed between the output end 115 and the photodetector 121.

In these three embodiments, the anti-reflective coating is optional on the surface of the output end after being cut or polished. The anti-reflective coating may further reduce the Fresnel reflection and eliminates the Fabry-Pérot fringes while increase the complexity of processing.

FIG. 6(*a*) shows the structure of the hollow-core photonic crystal fiber gas cell and the measured transmission spectra. The upper portion of FIG. 6(*a*) shows the structure of a conventional hollow-core photonic crystal fiber gas cell whose front and rear end surfaces are fusion spliced as flat ends with two optical fibers to form the gas cell; the lower portion of the FIG. 6(*a*) shows its transmission spectrum with obvious oscillations by the Fabry-Pérot fringes. FIG. 6(*b*) shows an embodiment of the hollow-core photonic crystal fiber gas cell and the measured transmission spectrum of the present invention. The upper portion of FIG. 6(*b*) shows the structure of the hollow-core photonic crystal fiber gas cell; the lower portion of the figure shows measured transmission spectrum with oscillations being eliminated.

The hollow-core photonic crystal fiber gas cell effectively alleviates the background noise of the transmitted light of the existing hollow-core photonic crystal fiber gas cells and has the characteristics of being small in size, light in weight, and high in stability.

Various embodiments have been described above. Although the invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

We claim:

1. A hollow-core photonic crystal fiber gas cell, comprising
    a single-mode fiber having two ends,
    a fiber splicing protection sleeve,
    a hollow-core photonic crystal fiber having two ends, and
    a photoelectric detector having a detection surface,
    wherein one end of the single-mode fiber is fused with one end of the hollow-core photonic crystal fiber to form a fusion splice and the end of a sealed hollow-core photonic crystal fiber gas cell;
    the fiber splicing protection sleeve covers and protects the fusion splice;
    the other end of the hollow-core photonic crystal fiber gas cell is processed into an output end in by fusion sealing, and an end surface of the output end faces, but is not parallel to, the detection surface of the photoelectric detector.

2. A method for preparing the hollow-core photonic crystal fiber gas cell as described in claim 1, comprising
    processing one end of the single-mode fiber by fusion splicing to form a fusion splice and sealing the end of the hollow-core photonic crystal fiber gas cell air-tight,
    covering and protecting the fusion splice with the fiber splicing protection sleeve,
    placing the hollow-core photonic crystal fiber and the single-mode fiber spliced thereto in a vacuum chamber,
    filling the vacuum chamber and the hollow-core of the hollow-core photonic crystal fiber with gas,
    causing the other end of the hollow-core photonic crystal fiber to be collapsed by fusing in the gas chamber and sealing the gas in the hollow-core,
    treating the collapsed end of the hollow-core photonic crystal fiber, and
    fixing the output end of the hollow-core photonic crystal fiber and the photodetector on a base plate,
    wherein the collapsed end of the hollow-core photonic crystal fiber is treated by passing a signal light into the other end of the single-mode fiber and receiving a transmitted light from the collapsed end, detecting the transmitted light by the photodetector, and recording the detected signal; and
    matching the detecting signal to requirements of the system by cutting, polishing, or coating the collapsed end of the hollow-core photonic crystal fiber, and the after machining collapsed end forms the output end of the hollow-core photonic crystal fiber.

* * * * *